United States Patent
Schwarzwaelder et al.

(10) Patent No.: US 8,709,389 B2
(45) Date of Patent: Apr. 29, 2014

(54) HAIR CARE COMPOSITION

(75) Inventors: Claudius Schwarzwaelder, Burghausen (DE); Michael Tobias Zarka, Burghausen (DE); Christian Hoegl, Reut (DE); Heidemarie Schwarzwaelder, Burghausen (DE)

(73) Assignee: Wacker Chemie AG, Munich (DE)

( * ) Notice: Subject to any disclaimer, the term of this patent is extended or adjusted under 35 U.S.C. 154(b) by 818 days.

(21) Appl. No.: 12/293,207

(22) PCT Filed: Feb. 28, 2007

(86) PCT No.: PCT/EP2007/051882
§ 371 (c)(1),
(2), (4) Date: Sep. 16, 2008

(87) PCT Pub. No.: WO2007/104645
PCT Pub. Date: Sep. 20, 2007

(65) Prior Publication Data
US 2009/0060858 A1 Mar. 5, 2009

(30) Foreign Application Priority Data
Mar. 16, 2006 (DE) .......... 10 2006 012 199

(51) Int. Cl.
*A61Q 5/12* (2006.01)
*A61K 8/00* (2006.01)
*A61K 8/18* (2006.01)
*A61Q 5/00* (2006.01)
*A61Q 9/00* (2006.01)
*A61K 8/72* (2006.01)
*A61Q 7/00* (2006.01)

(52) U.S. Cl.
USPC .......... 424/70.12; 424/70.1; 424/70.11

(58) Field of Classification Search
None
See application file for complete search history.

(56) References Cited

U.S. PATENT DOCUMENTS

| | | |
|---|---|---|
| 5,565,193 A | 10/1996 | Midha et al. |
| 5,618,524 A | 4/1997 | Bolich, Jr. et al. |
| 6,350,439 B1 | 2/2002 | Dupuis |
| 2002/0015681 A1 | 2/2002 | Carballada et al. |
| 2005/0143547 A1 | 6/2005 | Stark et al. |
| 2006/0074187 A1 | 4/2006 | Stark et al. |

FOREIGN PATENT DOCUMENTS

| | | | |
|---|---|---|---|
| EP | 0 408 311 A | 1/1991 | |
| EP | 0 412 704 A2 | 2/1991 | |
| EP | 0 412 704 B1 | 2/1991 | |
| JP | 2001-048985 A | 2/2001 | |
| JP | 2001048985 A * | 2/2001 | .......... A61K 8/00 |
| WO | 95/00106 A1 | 1/1995 | |
| WO | 99/55294 A1 | 11/1999 | |
| WO | 00/51557 A1 | 9/2000 | |
| WO | 03/085035 A1 | 10/2003 | |
| WO | 2004/065437 A1 | 8/2004 | |

OTHER PUBLICATIONS

Machine translation of Ito et al., JP 2001/048985 A, published Feb. 20, 2001, translated on Oct. 14, 2011.*
Jachowicz et al., "Mechanical analysis of elasticity and flexibility of virgin and polymer-treated hair fiber assemblies," J. Cosmet. Sci., 53, pp. 345-361 (Nov./Dec. 2002).
Lochhead, R.Y., "The History of Polymers in Hair Care (1940-Present)," Cosmetics & Toiletries, V. 103, Dec. 1988 (pp. 23-61).
Jachowicz et al., "Dynamic hairspray analysis. I. Instrumentation and preliminary results," J. Soc. Cosmet. Chem., 47, pp. 73-84 (Mar./Apr. 1996).
Jachowicz et al., "Dynamic hairspray analysis. II. Effect of polymer, hair type, and solvent composition," J. Soc. Cosmet. Chem., 52, pp. 281-295 (Sep./Oct. 2001).

* cited by examiner

*Primary Examiner* — Gina C Justice
*Assistant Examiner* — Michael B Pallay
(74) *Attorney, Agent, or Firm* — Brooks Kushman P.C.

(57) ABSTRACT

Hair care compositions contain from 0.1 to 12 weight percent of a silicone copolymer or saponification product thereof, prepared from silicones, at least 10% of which contain polymerizable groups, 0.5-14% of hydrophilic comonomers, and 30-99.9% of hydrophobic comonomers. The compositions exhibit good hair care properties.

8 Claims, 2 Drawing Sheets

HAIR CARE COMPOSITION

CROSS-REFERENCE TO RELATED APPLICATION

This application is the U.S. national phase of PCT Appln. No. PCT/EP2007/051882 filed Feb. 28, 2007 which claims priority to German application DE 10 2006 012 199.6 filed Mar. 16, 2006.

BACKGROUND OF THE INVENTION

1. Field of the Invention

This invention relates to hair care compositions with improved application properties and improved properties combining hold, flexibility and soft feel.

2. Description of the Related Art

The publications The History of Polymers in Hair Care (1940-present) and R. Y. Lochhead, Cosmetic & Toiletries, p. 23, 103 (1988) show that the development of hair styles and hair styling products has for a long time been influenced by the development of polymers and shaped by their novel properties.

From shellac to PVP, the properties have been adjusted to the desired hair styling effects and continually improved primarily through the use of copolymers in a targeted manner, through the individual monomer building blocks. Classic examples are the PVA/PVP copolymers in which hygroscopicity of the PVP is adjusted to an advantageous level through incorporation of vinyl acetates.

This constant development was also accompanied by more and more requirements which novel products have to satisfy. Examples of such requirements on a hair care composition are improved hold of the hair style (better setting), no sticky feel, no rigid hair, rapid drying times, ease of combing, hair volume, no weighing down of the hair, no water absorption through the polymer, ease of application in wet hair, ease of washing out with a shampoo and no flaking of the polymer film during combing.

On account of the multitude of requirements placed on such a product, sometimes with contradictory properties, it is therefore no wonder that there is a multitude of polymers for hair styling applications.

One dominant problem is the combination of good setting of the hair style and simultaneous nonsticky—or better—soft/natural feel of the hair. Especially if polymers for strong hold, such as acrylates, acetates, methyl vinyl ether/maleic anhydride or PVP, are used.

In order to achieve a flexible hold which still allows the hair style to move naturally and does not produce rigid hair with a brittle polymer film, copolymers of a combination of part acrylate and part silicone are used, where the highly flexible silicone part also affords a soft feel as well as high hydrophobicity.

There have been various approaches for achieving the combination of these building blocks and they have been described for hair styling applications, in particular hair spray applications.

Thus, the application EP 0 408 411A2 claims silicone copolymers with at least 15% by weight of hydrophilic monomer, for example, a dimethylaminoethyl methacrylate, in order to achieve setting. The U.S. Pat. No. 5,565,193 describes a formulation which additionally also comprises 0.5 to 15% by weight of a hydrocarbon solvent which has a boiling point of >105° C. The specifications WO 95/00106 and WO 99/55294 describe formulations with a water content of at most 10%. In addition, further patent specifications U.S. Pat. No. 6,350,439 B1, US 2002/0015681 A1, U.S. Pat. No. 5,618,524 and EP 0 412 704 B1 and also WO 00/51557 describe graft copolymers with monofunctional silicone macromonomers for use in hair styling products which achieve the combination effect described above.

Although these hair spray formulations containing silicone copolymers already lead to a certain improvement in the combination of good setting and styling with more pleasant soft hair feel, a further improvement in the individual effects in combination is required since it is requested by the consumer. Since, in addition to the chemical blocks which make up the hair styling polymers and can thus be brought to bear an influence on setting and soft feel, also the rheological behaviour of the hair spray solution, the droplet size of the spray and the viscosity of the polymer solution droplet have a great influence on the desired effects, a composition has to be found which leads to an improvement in the parameters and thus to an increase in the effects of setting and hold.

Low-viscosity compositions distribute themselves more readily on the hair surface on account of their better spreading. It is known that the lower the viscosity of the hair spray formulation on the hair, the more unnoticeable the sticky sensation and the more pleasant the hair feels.

A low viscosity of the hair spray solution, however, leads to relatively small droplet sizes during the spraying operation. Small droplets achieve weaker setting between the individual hair fibers and thus lower hold of the fibers, whereas larger droplets contribute to stronger setting and thus to a better hold of the hair style.

Optimal hair sprays are thus those which have large droplets during spraying but have a polymer solution with low viscosity that reaches the hair.

The droplet size can be adjusted to a certain degree through appropriate choice of valves and spray heads. Ultimately, however, the rheological parameters of the polymer solution and of the polymer film influence the principal improvement in the effects.

In order to achieve an improvement in the setting and flexibility while taking into account the described problems, the inventors in WO 00/51557 and US 2002/0015681 A1 describe a composition which comprises a combination of two different silicone graft copolymers. As a result, the composition has a high viscosity if it is released from the spray container with high shear, and a low viscosity when it reaches the hair and is subjected to low shear. However, a disadvantage here is that two different polymers have to be used for the formulation. The polymers have a high molecular weight, which leads to high solution viscosities and thus to difficult processing. The use of a single polymer which additionally has a lower molecular weight range would therefore be desirable.

SUMMARY OF THE INVENTION

It was therefore an object of this invention to provide a hair care composition which has both improved processing properties during production and also improved application properties combining hold, flexibility and soft feel.

These and other objects are provided by hair care compositions which comprise 0.1-12% by weight of at least one silicone copolymer and/or saponification products thereof, which consists of
  A) 0.1-50% of one or more silicones, where 10-100% of these silicones have at least two polymerizable groups,
  B) 0.5-14% of one or more hydrophilic monomers and
  C) 30-99.4% of one or more hydrophobic monomers.

Figure 1:
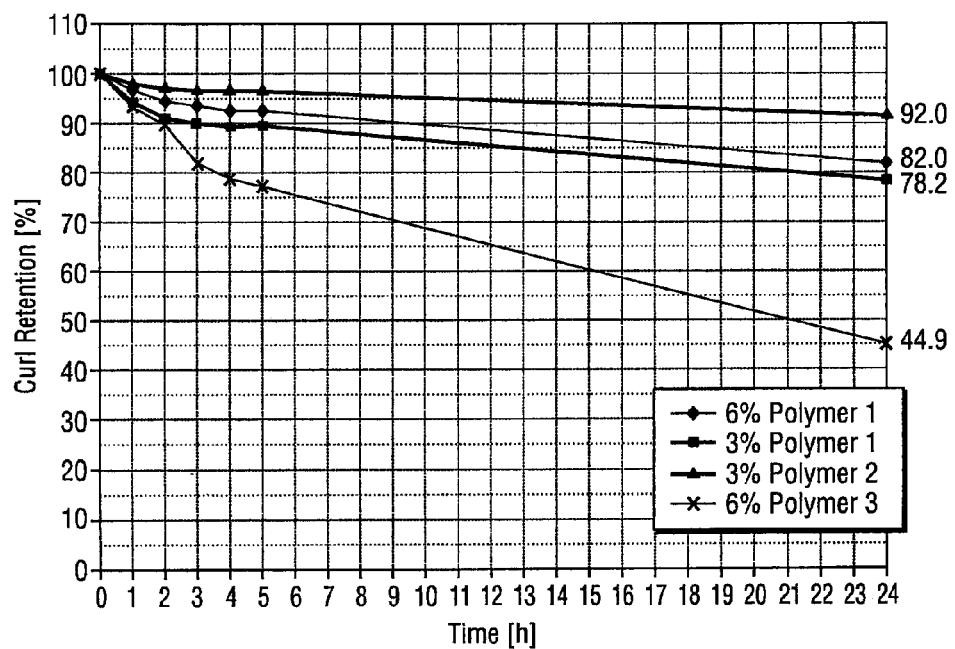
FIG. 1 illustrates the benefits regarding curl retention for three embodiments of the present invention compared to a non-inventive composition.
Figure 2:
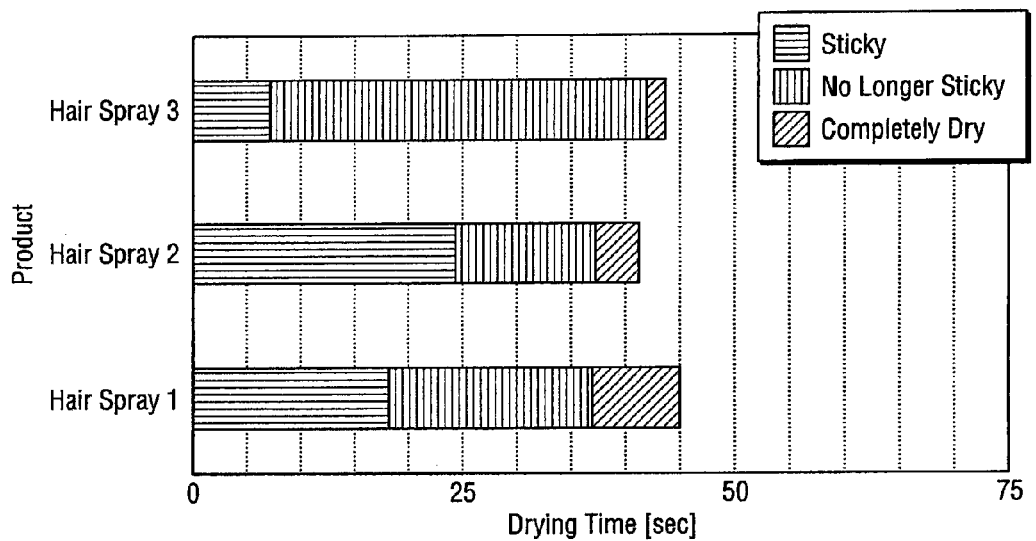
FIG. 2 illustrates the benefits of two embodiments of the present invention with regard to stickiness and drying time.

Preferably, the silicone copolymer consists of 0.1-40% of silicone A).

This type of silicone copolymer and a method for its production have already been described in the patent specification WO 03/085035 A1, the disclosure of which in this regard should also be subject matter of this application. However, it has unexpectedly been found that the auxiliary monomers described merely as optional in WO 03/085035 A1 are absolutely necessary for the hair care composition according to the invention since only 0.5-14%, preferably 0.5-10%, most preferably 3-6%, of hydrophilic monomers B) make a significant contribution to actually improving the properties combining hold, flexibility and soft feel.

To produce the saponification products, the silicone copolymer is saponified in a manner known to the person skilled in the art, in alcoholic solution, using the acidic or alkaline catalysts customary for this purpose. Suitable solvents are aliphatic alcohols having 1 to 6 carbon atoms, preferably methanol or ethanol. The saponification can, however, also be carried out in a mixture consisting of water and aliphatic alcohol. Acidic catalysts are, for example, strong mineral acids such as hydrochloric acid or sulfuric acid, or strong organic acids such as aliphatic or aromatic sulfonic acids. Preference is given to using alkaline catalysts. These are, for example, the hydroxides, alkoxides and carbonates of alkali metals or alkaline earth metals. The catalysts are used in the form of their aqueous or alcoholic solutions. The amounts of alkaline catalyst used are generally 0.2 to 20.0 mol %, based on silicone organopolymer.

The saponification is generally carried out at temperatures of from 20° C. to 70° C., preferably 30° C. to 60° C. The addition of the catalyst solution initiates the transesterification. Upon reaching the desired degree of hydrolysis, generally between 40 and 100 mol %, the transesterification is terminated. In the case of the acid-catalyzed transesterification, termination takes place by adding alkaline reagents. In the case of the preferred alkali-catalyzed transesterification, termination takes place by adding acidic reagents, such as carboxylic acids or mineral acids. When the saponification reaction is complete, the product is separated off from the liquid phase. This can take place by means of customary devices for solid/liquid separation, for example by means of centrifugation or filtration.

Preference is given to hair care compositions with silicone copolymers and/or saponification products thereof consisting of:
  A) 0.1-50% of one or more silicones, where at least 50% of the silicones have two polymerizable groups on the chain ends.
  B) 0.5-14% of one or more hydrophilic monomers
  C) 30-99.4% of a vinyl ester or an ester of acrylic acid or methacrylic acid as hydrophobic monomer and optionally further hydrophobic monomers.

Particular preference is given to hair care compositions with silicone copolymers and/or saponification products thereof consisting of:
  A) 0.1-40% of one or more silicone macromonomers with the general formula (1):

$$R^1R_2SiO(SiR_2O)_nSiR_2R^1 \qquad (1)$$

where
R each independently, is a monovalent, linear or cyclic, Si—C-bonded, optionally substituted hydrocarbon radical or an alkoxy radical having 1 to 18 carbon atom(s) per radical,
$R^1$ is a polymerizable group, and
n is 10 to 1000;
  B) 0.5-10% of a free-radically polymerizable carboxylic acid selected from among crotonic acid or acrylic acid, and optionally further hydrophilic monomers
  C) 30-99.4% of vinyl acetate as hydrophobic monomer and optionally further hydrophobic monomers.

The silicone copolymers according to the invention can be synthesized, for example, in a free-radical solution polymerization in a solvent or solvent mixture that has good dissolution properties both for the silicone fraction and also for the organic fraction and at the same time acts as molecular weight regulator.

The silicone copolymers obtained by this preferred method are characterized by high transparency and lack of phase separation. Using transmission electron microscopy, either no discrete silicone domains or only very small silicone domains of less than 300 nm can be detected in the continuous matrix. Surprisingly, it has been found that the silicone copolymers again have significantly improved properties in the combination of hold and soft feel compared to the phase-separated silicone graft copolymers known, for example, from EP 0 412 704 B1.

The hair care composition according to the invention exhibits its advantages particularly in the case of hair styling applications since it overcomes the limitations discussed previously, and; through its composition, also makes accessible formulations which permit the seemingly contradictory connection between large droplets during the spraying operation and low viscosity on the hair fiber, while the hair spray applications permit good hold and good soft hair feel through the use of at least one individual silicone copolymer. A further advantage is the possibility of an aqueous formulation with a fraction of less than 15% of hydrophilic monomer B). This likewise leads to an increase in the soft feel and the flexibility.

Furthermore, the silicone copolymers according to the invention offer the advantage of formulating in particular also environmentally friendly aerosol and pump spray formulations with a water content of at least 10% without requiring an additional hydrocarbon as solvent with a boiling point of more than 105° C.

The hair care composition comprises 0.1-12% by weight of at least one of the silicone copolymers according to the invention and/or saponification products thereof. Particular preference is given to the range 2-8% by weight and very particular preference to 2.5-6% by weight.

In the silicone copolymer according to the invention, through the use of di- and/or multifunctional silicone macromonomers A), the organic polymer chains are covalently bridged by silicone chains. It is essential to the invention that the formation of insoluble networks is prevented. This occurs in the manner known to the person skilled in the art, for example by controlling the molecular weight and/or adapting the solids content during the polymerization. Preferably, the silicone copolymers according to the invention exhibit a molecular weight Mw of at least 30,000 g/mol. Furthermore, the molecular weight Mw is preferably at most 90,000 g/mol. The molecular weight Mw is most preferably between 35,000-60,000 g/mol. The organic blocks here are composed of different monomers. They comprise both hydrophilic monomers B) and also hydrophobic monomers C).

Suitable silicones A) are linear or branched polysiloxanes with a chain length of from 10 to 1000, where at least 10% of the silicones used have two or more free-radically polymerizable groups. Preferably, at least 50% of the silicones A) have two polymerizable groups on the chain ends.

Particular preference is given to at least one silicone A) which corresponds to the general formula (2)

$$R^1{}_a R_{3-a} SiO(SiR_2O)_n RiR_{3-a} R^1 a' \quad (2)$$

where
R is identical or different, and is a monovalent, optionally substituted, linear or branched alkyl radical or alkoxy radical having in each case 1 to 18 carbon atoms, such as, for example, methyl, ethyl, n-propyl, isopropyl, 1-n-butyl, 2-n-butyl, isobutyl, tert-butyl, n-pentyl, isopentyl, neopentyl, tert-pentyl, hexyl radicals etc, alkoxy radicals, such as, for example, methoxy, ethoxy, propoxy, n-butyloxy etc. Alkyl and alkoxy radicals R can sometimes also be substituted by other radicals such as halogen, mercapto, carboxyl, keto, enamine, amino, aminoethylamino, aryloxy, aryl, alkoxysilyl or hydroxyl radicals.
$R^1$ is a polymerizable group,
a and a', independently of one another, are 0 or 1,
n=10 to 1000,
with the proviso that at least 10% of the silicones A) used have two polymerizable groups.

Suitable polymerizable radicals R1 are alkenyl radicals having 2-8 carbon atoms. Examples are polymerizable groups such as vinyl, allyl, butenyl, acryloyloxyalkyl, and methacryloyloxyalkyl groups, the alkyl radicals here comprising 1-4 carbon atoms. Preference is given to vinyl groups, 3-methacryloyloxypropyl, acryloyloxymethyl and 3-acryloyloxypropyl groups, such as, for example, α,ω-divinylpolydimethylsiloxanes, α,ω-di(3-acryloxypropyl)polydimethylsiloxanes, α,ω-di(3-methacryloxypropyl)-polydimethylsiloxanes, α-monovinylpolydimethylsiloxanes, α-mono(3-acryloxypropyl)polydimethylsiloxanes, α-mono(acryloxymethyl) polydimethylsiloxanes, and α-mono(3-methacryloxypropyl) polydimethylsiloxanes.

Most preferred silicones A are type-pure α,ω-divinylpolydimethylsiloxanes of the general formula $CH_2$=CH—$SiMe_2$ ($SiMe_2O)_n SiMe_2$-CH=$CH_2$, which are sold, for example, by Wacker Chemie A G, Munich, Germany under the tradename Polymer PTS-P 1000, or α,ω)-dimethacryloxypropylpolydimethylsiloxanes of the general formula $CH_2$=$C(CH_3)$ CO—O—$(CH_2)_3$—$SiMe_2(SiMe_2O)SiMe_2$-$(CH_2)_3$—O—CO—$(CH_3)C$=$CH_2$, where n has the meaning given above.

Suitable hydrophilic monomers B) are, for example, unsaturated organic mono- and polycarboxylic acids such as acrylic acid, methacrylic acid, and crotonic acid, and dicarboxylic acids such as fumaric acid, and unsaturated organic acid anhydrides, for example maleic anhydride, unsaturated alkyl methacrylates and mixtures thereof.

However, others are also suitable as hydrophilic monomers B), such as unsaturated carboxamides and carbonitriles, for example acrylamide and acrylonitrile, and also unsaturated sulfonic acids and salts thereof, such as, for example, vinylsulfonic acid and 2-acrylamido-2-methylpropanesulfonic acid. Cationic monomers such as diallyldimethylammonium chloride (DADMAC), 3-trimethylammonium propyl(meth) acrylamide chloride (MAPTAC) and trimethylammonium ethyl(meth)acrylate chloride. Particular preference is given to crotonic acid, acrylic acid and methacrylic acid.

The silicone copolymer and/or saponification product thereof consists preferably of 0.5-10%, particularly preferably of 3-6%, of hydrophilic monomer B).

Suitable hydrophobic monomers C) are, for example, unsaturated alcohols and esters thereof, such as, for example, vinyl esters of branched and unbranched alkylcarboxylic acids having 1-15 carbon atoms. Particular preference is given to vinyl acetate, vinyl propionate, vinyl butyrate, vinyl 2-ethylhexanoate, vinyl laurate, 1-methylvinyl acetate, vinyl pivalate and vinyl esters of alpha-branched monocarboxylic acids having 5-11 carbon atoms, such as, for example, VeoVa9® and VeoVa10® (trademarks of Hexion Specialty Chemicals, Columbus, Ohio, USA). Vinyl acetate is most preferred.

Further hydrophobic monomers C) may be unsaturated hydrocarbons such as ethane, propene, or butene and isobutanes.

In addition, the following substances are also suitable as hydrophobic monomers C): acrylic acid and methacrylic acid esters and mixtures thereof such as esters of branched and unbranched alcohols with hydrocarbon atoms of from $C_{1-15}$. In this connection, particular preference is given to methyl methacrylate, methyl acrylate, ethyl acrylate, ethyl methacrylate, propyl acrylate, propyl methacrylate, n-, iso- and t-butyl acrylate, n-, iso- and t-butyl methacrylate, 2-ethylhexyl acrylate and norbornyl acrylate. Likewise the diesters of fumaric acid and maleic acid, such as, for example, diethyl and diisopropyl esters are also suitable.

Especially for aerosol hair sprays with an environmentally friendly composition, for example for use in the USA, systems with a low content of organic volatile ingredients (low volatile organic compound—abbreviation—VOC) have to be developed on account of the Clean Air Act. This circumstance makes aqueous systems particularly interesting.

Furthermore, for a simple application on/in wet hair, the solvent should be miscible with water and the styling polymer should not exhibit phase separation or be precipitated if water is introduced into the system.

It is therefore preferable to select an aqueous solvent in order to permit easy applicability in wet hair, and to limit the fraction of volatile, organic components.

The hair spray composition comprises a suitable solvent or solvent mixture which comprises more than about 3% water and is present in the spray composition between 25-98%.

Aqueous-alcoholic solvent mixtures comprise at least 2.94-88% water and 12-97.06% of an alcohol or mixtures of alcohols and alcohol-soluble cosmetically acceptable solvents, such as silicones, alkanes and branched alkanes, alkyl carbonates, alkyl lactates, acetone, dialkyl ethers or alkyl esters. The following may be listed by way of example but are not limiting: ethanol, isopropanol, pentanes, linear volatile silicones, such as, for example, Wacker-BelsilDM 1 plus, SLM 38032, SLM 28033 and SLM 38038 or cyclic silicones, such as Wacker-Belsil CM040 (Wacker Chemie AG, Munich, Germany), dicaprylyl carbonate or butyl lactate.

Preference is given to solution mixtures of 15-60% water and 40-85% ethanol.

The silicone copolymers used in which, as hydrophilic monomers, representatives with acid functions have been used, must be neutralized or partially neutralized from 40-100% in the hair spray applications. The range from 70-100% is preferred. The bases used for the neutralization are organic bases, such as amino alcohols, such as 2-amino-2-methyl-1-propanol. Besides the organic bases, it is also possible to use inorganic bases such as potassium hydroxide. Mixtures of inorganic and organic bases can also be used. The amount of base which is required for the desired degree of neutralization of the polymer can be calculated using the equation (I)

$$B[g] = \frac{S[mg/g] * b[g/mol] * N/100 * P[g]}{56.11[g/mol] * c/100 * 1000} = \frac{S*b*N}{56.11*c*1000} \quad (I)$$

where
B=base in g
S=acid number of the polymer [mg of KOH/g of polymer]
P=amount of polymer [g]
b=molecular weight of the base [g/mol]
c=concentration of the base [%]
N=degree of neutralization [%].

No propellant gas is necessary in pump spray applications. Here, only the solvent is required together with the customary ingredients, such as neutralization agent and further auxiliaries.

For aerosols, 20-50% of a propellant gas suitable for cosmetic hair applications are used in the hair spray composition. Customary propellant gases from the series of hydrocarbons such as propane, butane and isobutane, and also non-hydrocarbon-type propellant gases, such as, for example, dimethyl ether, carbon dioxide and nitrogen and mixtures thereof are all useful. Dimethyl ether is used as the preferred propellant gas.

The hair care composition can comprise further additives selected from the group comprising anionic, cationic or nonionic surfactants, perfumes, photoprotective filters, preservatives, corrosion inhibitors, proteins, vitamins, polymers, vegetable, synthetic or mineral oils and any desired other additive classically used in cosmetic compositions, comprising, for example, softeners for varying and adjusting the film properties, for example, stearates, citrates, polyether-functional silicones, aryl-functional silicones, glycerol, fatty alcohols, oleates, phthalates, glycols, or conditioners such as fatty alcohols, other silicone fluids and resins, aryl-containing silicones for improving shine, for example, phenyltrimethicones, trimethylsiloxyphenyldimethicones with a refractive index of >1.46, or conditioning agents which impart volume to the hair style.

The preparation of the hair care composition according to the invention takes place according to methods known to the person skilled in the art and is characterized in that all of the components are mixed with 0.1-12% by weight of the silicone copolymer according to the invention and/or its saponification product which consists of A) 0.1-50% of one or more silicones, where at least 10% of these silicones have at least two polymerizable groups,
B) 0.5-14% of one or more hydrophilic monomers and
C) 30-99.4% of one or more hydrophobic monomers.

The hair care compositions according to the invention are used in the form of a hair spray, styling mousse, styling gel, shampoo, hair rinse, hair treatment, lotion or cream.

EXAMPLES

Preparation of the Silicone Copolymer 1 (According to the Invention)

39.95 kg of ethyl acetate, 3.01 kg of isopropanol, 10.19 kg of polymer PTS-P 1000, 1.11 kg of crotonic acid, 0.492 kg of VeoVa 10, 3.05 kg of vinyl acetate and 0.193 kg of polyphenylvinylene=PPV (tert-butyl perpivalate, 75% strength solution in aliphatics) are initially introduced into a 150 l stirred-tank reactor with anchor stirrer, reflux condenser and metering devices. The mixture is heated to 70° C. with stirring (start of reaction). Ten minutes after the start of the reaction, the metered addition of a mixture of 1.11 kg of crotonic acid, 3.94 kg of VeoVa 10 and 24.41 kg of vinyl acetate is run in. The monomer metered addition takes place at a steady metering rate and lasts for a period of 4 h. Thirty minutes after the start of the reaction, 0.075 kg of PPV are added. Further batchwise metered additions of the initiator take place at intervals of 30 minutes over a period of 5 h (in each case 0.075 kg of PPV, last batchwise metered addition 5 h after the start of the reaction). Following the last initiator addition, the mixture is afterpolymerized for a further 2 h at 70° C. The mixture is then heated for distillation. The resulting polymer melt is discharged at a temperature of about 130° C.

Analyses: acid number 30.6 mg of KOH/g, viscosity (Höppler, 10% strength solution in ethyl acetate)=2.0 mPas, SEC $M_w$=42,414, $M_n$=8716, polydispersity 4.87, $T_g$=39.2° C.

Preparation of the Silicone Copolymer 2 (According to the Invention)

649.77 g of ethyl acetate, 48.91 g of isopropanol, 251.09 g of polymer PTS-P 1000, 27.29 g of crotonic acid, 12.12 g of VeoVa 10, 75.13 g of vinyl acetate and 4.77 g of PPV are initially introduced into a 3 l laboratory reactor. The mixture is heated to 70° C. with stirring (start of the reaction). Ten minutes after the start of the reaction, the metered addition of a mixture of 27.29 g of crotonic acid, 97.05 g of VeoVa 10 and 601.71 g of vinyl acetate is run in. The monomer metered addition takes place at a steady metering rate and lasts for a period of 4 h. Thirty minutes after the start of the reaction, 1.85 g of PPV are added. Further batchwise metered additions of the initiator take place at intervals of 30 min over a period of 5 h (in each case 1.85 g of PPV, last batchwise metered addition 5 h after the start of reaction). After the last initiator addition, the mixture is afterpolymerized for a further 2 h at 70° C. The mixture is then heated for distillation.

Analyses: acid number 32.4 mg of KOH/g, viscosity (Höppler, 10% strength solution in ethyl acetate)=2.4 mPas, SEC $M_w$=86,605, $M_n$=11,567 polydispersity 7.49, $T_g$=37.9° C.

Preparation of the Silicone Polymer 3 (not According to the Invention)

31.59 kg of ethyl acetate, 5.88 kg of isopropanol, 0.208 kg of Dehesive™ 919, 1.47 kg of vinyl acetate and 0.022 kg of PPV are initially introduced into a 150 l stirred-tank reactor with anchor stirrer, reflux condenser and metering devices. The mixture is heated to 70° C. with stirring (start of the reaction). After reaching an internal temperature of 70° C., the initiator metered addition (0.107 kg of PPV in 2.76 kg of ethyl acetate) over 310 minutes is started. Ten minutes after the start of the reaction, the monomer metered addition (3.27 kg of Dehesive 929, 11.76 kg of vinyl acetate) over 4 h is started. When the two metered additions are complete, the mixture is fully polymerized for a further two hours at 70° C. The mixture is then heated for distillation. The resulting polymer melt is discharged at a temperature of about 130° C. Analyses: acid number 0.561 mg of KOH/g, viscosity (Höppler, 10% strength solution in ethyl acetate)=1.33 mPas, SEC $M_w$=14,255, $M_n$=4912, polydispersity 2.90, $T_g$=27.0° C.

Preparation of the Silicone Copolymer 4 (According to the Invention)

26.47 kg of ethyl acetate, 5.57 kg of isopropanol, 4.43 kg of VIPO 300, 2.33 kg of crotonic acid, 2.61 kg of VeoVa 10, 11.19 kg of vinyl acetate and 0.163 kg of PPV are initially introduced into a 150 l stirred-tank reactor with anchor stirrer, reflux condenser and metering devices. The mixture is heated to 70° C. (start of the reaction). At the start of the reaction, the metered addition of 0.63 kg of PPV in 5.59 kg of ethyl acetate over a period of 510 min is started. Ten minutes after the start of the reaction, the metered addition of a mixture of 1.40 kg of crotonic acid, 1.12 kg of VeoVa 10, 5.59 kg of vinyl acetate and 2.98 kg of VIPO 300 (an $\alpha,\omega$-divinylsilicone with mean chain length 133) is run in. The monomer metered addition takes place at a steady metering rate and lasts for a period of 120 minutes. 20 minutes after the end of this monomer metered addition, a further monomer addition (5.59 kg of vinyl acetate, 1.17 kg of VIPO 300) over 300 minutes is started. When all of the metered additions are complete, the mixture is after polymerized for a further 2 h at 70° C. The mixture is then heated for distillation.

Analyses: acid number 67.1 mg of KOH/g, viscosity (Höppler, 10% strength solution in ethyl acetate)=1.5 mPas, SEC $M_w$=26,049, $M_n$=7670 polydispersity 3.4, $T_g$=46.0° C.

The above-described silicone copolymers 1, 2, 3 and 4 are used below in hair styling formulations/compositions. These examples below are basic formulations which can be expanded with further additives, as listed above, in accordance with customary concentrations known to the person skilled in the art.

Preparation of Aerosol Hair Spray: Silicone Copolymers are dissolved with stirring in the solvent or solvent mixture, such as, for example, water/ethanol. In the case of silicone copolymers which carry acid groups, the corresponding amount of base, such as, for example, aminomethylpropanol—which has been calculated according to degree of neutralization—is firstly added to the solvent or solvent mixture. The silicone copolymer is then dissolved with stirring. Upon adding further additives, these are likewise dissolved with stirring. Depending on the additive, the solution is obtained more quickly by heating up to 40° C.

The resulting polymer solution is bottled into the aerosol cans and equipped with the corresponding propellant gas or propellant gas mixture in an aerosol bottling plant.

The preparation of pump hair spray takes place analogously. However, no propellant gas is required. The polymer solutions are bottled into pump spray packagings.

Example 1

Aerosol Hair Spray with 3% by Weight of Silicone Copolymer

The composition of the hair spray is given in table 1.

TABLE 1

| Substance | Concentration [% by wt.] |
| --- | --- |
| Ethanol | 34.43 |
| Aminomethylpropanol 30% strength | 0.46 |
| Water | 22.11 |
| Silicone copolymer 1 or 2 or 3 | 3.00 |
| Dimethyl ether | 40.00 |

Example 2

Aerosol Hair Spray with 4.5% by Weight of Silicone Copolymer

The composition of these hair sprays is given in table 2.

TABLE 2

| Substance | Concentration [% by wt.] |
| --- | --- |
| Ethanol | 33.33 |
| Aminomethylpropanol 30% strength | 0.67 |
| Water | 21.50 |
| Silicone copolymer 1 or 2 or 3 | 4.50 |
| Dimethyl ether | 40 |

Example 3

Aerosol Hair Spray with 6% by Weight of Silicone Copolymer

The composition of these hair sprays is given in table 3.

TABLE 3

| Substance | Concentration [% by wt.] |
| --- | --- |
| Ethanol | 37.58 |
| Aminomethylpropanol 30% strength | 0.35 |
| Water | 24.07 |
| Silicone copolymer 1 or 2 or 3 | 6.00 |
| Dimethyl ether | 32.00 |

Example 4

Pump Hair Sprays with 10% by Weight of Silicone Copolymer

The composition of these pump hair sprays is given in table 4.

TABLE 4

| Substance | Concentration [% by wt.] |
| --- | --- |
| Ethanol | 54.30 |
| Aminomethylpropanol 30% strength | 0.80 |
| Water | 34.90 |
| Silicone copolymer 1 or 2 or 3 | 10.00 |

Preparation of Styling Mousse:

The base, such as, for example, aminomethylpropanol, is dissolved together with the emulsifier, such as, for example, PEG-40 hydrogenated castor oil, in water with stirring. This mixture is heated to a maximum of 50° C. and the silicone copolymer is dissolved therein in portions with stirring. Depending on the sensitivity to heat, further additives are added at 50° C. or after cooling at room temperature and dissolved with further stirring. The cooled solution is bottled in cans and equipped with the propellant gas or propellant gas mixture.

Example 5

Styling Mousse with 3% by Weight of Silicone Copolymer

The composition of this styling mousse is given in table 5.

TABLE 5

| Substance | Concentration [% by wt.] |
|---|---|
| Aminomethylpropanol 30% strength | 1.06 |
| Water | 74.80 |
| PEG-40 hydrogenated castor oil (Cremophor RH 40 from BASF AG, Ludwigshafen, Germany) | 0.50 |
| Silicone copolymer 4 | 3.00 |
| Polyquaternium-10 (UCARE Polymer JR 400 from Amerchol Corporation, Piscataway, USA) | 0.80 |
| Amodimethicone, Cetrimonium Chloride, Trideceth-10 (Wacker-Belsil ® ADM 6057 E, from Wacker Chemie AG, Munich, Germany) | 0.30 |
| Cocamidopropylbetaine (Genagem CAB 818 30% from Clariant GmbGH, Frankfurt, Germany) | 11.04 |
| Phenoxyethanol, methylparaben, ethylparaben, butylparaben, propylparaben and isobutylparaben (Phenonip from Schülke & Mayr GmbH, Horderstedt, Germany) | 0.50 |
| Propane/butane | 8.00 |

The hair care compositions obtained in this way were subjected to various tests which show their properties on hair.

Curl Retention

On this model for ascertaining hair setting at high atmospheric humidities, the percentage changes between starting length and finishing length of curls prepared in a defined way compared to hair tress length are recorded. The curl retention properties of hair styling products are monitored at 23° C. and 90% relative atmospheric humidity over a period of 24 hours.

Hair tresses 15 cm in length are gathered into bundles of 3.5 g from European brown hair and tied using a binding thread and permanently fixed using a suitable adhesive. The hair tresses are washed with shampoo and rinsed with completely demineralised (=DEM) water. The hair tresses are combed and wound onto a plastic rod with a diameter of 1.4 cm, fixed temporarily with a sheath and dried overnight at 50° C. The curls are carefully slid off from the plastic rods and, after cooling, sprayed evenly with the spray to be tested. After a drying phase of one hour at room temperature, the curls are fastened to a graduated hanging device in a climatically controlled cabinet at 23° C. and 90% relative atmospheric humidity. The starting length of the curl was determined and noted beforehand. At certain time intervals, the curl lengths, i.e. the change relative to the starting length, are read off over a period of 24 h.

The calculation is made according to equation (II)

$$\% \text{ CURL RETENTION} = \frac{L - L_t}{L - L_0} \times 100 \quad \text{(II)}$$

where
$L$=length of the hair tress
$L_o$=starting length of the curl
$L_t$=length of the curl after/during measurement.

FIG. 1 shows by way of example the results of this test for the examples 1 according to the invention with 3% by weight of silicone copolymer 1 and 2, and also example 3 with 6% by weight of silicone copolymer 1 compared to noninventive example 3 with 6% by weight of silicone copolymer 3.

Further experiments carried out analogously showed that silicone copolymers according to the invention exhibit good curl retention values at use concentrations of 2-12% by weight. Particularly above 3% by weight, very good hold at high atmospheric humidity is obtained, which still produces curl retention results in the range 75-95% even after 24 h. By contrast, noninventive example 3 with 6% by weight of silicone copolymer 3 shows a very great drop to about 45% within this time.

Elasticity/Flexibility/Plasticity

To determine and assess the flexibility and elasticity of the polymer film in the hair, the three-point flexural rigidity is determined. Hair tresses of brown European hair 20 cm in length are washed and dried. The hair is sprayed evenly with aerosol sprays at a distance of 20 cm for 3 sec. on each side. When using a pump spray, 10 strokes are made on each side. 5 tresses are used per product. The treated tresses are conditioned for 24 h in a climatically controlled room.

The investigations of the hair compositions according to the invention reveal a very flexible polymer film which has very good elastic behaviour. The results can produce ideal values of 1.00 or are very close to the ideal value for elastic and flexible behaviour as described in the literature. Details of the measuring apparatus and of the measurement method are known to the person skilled in the art and are described for example in the following literature references, the disclosure of which in this regard are also subject matter of this application: Dynamic hairspray analysis. I. Instrumentation and preliminary results, J. Jachowicz, Y. Kao, J. SOC. COSMET. CHEM, p. 73, 47 (1996); Dynamic hair spray analysis II. Effect of polymer, hair type, and solvent composition, J. Jachowicz, Y. Kao, J. SOC. COSMET. CHEM, p. 281, 52 (2001); Mechanical analysis of elasticity and flexibility of virgin and polymer-treated hair fiber assemblies, J. Jachowicz, R. McMullen, J. COSMET. SCI., p. 34.5, 53 (2002).

Stickiness and Drying Time

While applying a hair spray, some of the solvent escapes or volatilizes. Within this time, the sensation upon touching the hair also changes from sticky and non-sticky. The effect is based on the softening function of the solvent and depends on various factors such as, for example, weight of the spray, temperature and air circulation. In this simple test, the specified factors are kept constant in order to permit a comparison between various formulations. Hair tresses of brown European hair with a length of 15 cm and a weight of 3.5 g are used. The hair tress is sprayed for 4 seconds from a distance of 10 cm and rotated in the process. Directly after the spraying operation, the tresses are repeatedly touched from top to bottom until the hair tress is perceived as completely dry. During this, the following times are registered:
a) time from the start until the hair tress is perceived as sticky
b) time from the start until the hair tress is no longer perceived as sticky
c) time from the start until the hair tress is evaluated as completely dry.

The tests are repeated several times. FIG. 1 shows the results for 5 examples. Hair spray 1 corresponds to example formulation 3 in which silicone copolymer 3 was used. Hair spray 2 corresponds to example formulation 1 in which silicone copolymer 1 was used and hair spray 3 corresponds to example formulation 3 in which silicone copolymer 1 was used.

In the panel test, rapid drying times of the examples according to the invention are found. The time phase in which the sprayed hair is perceived as sticky is very short, with a time between 20-30 seconds, despite a relatively high water content in the formulations.

Panel Test

In a panel test, 12 test subjects each receive 6 treated hair tresses each of 20 cm and 3.5 g of brown European hair. The hair tresses are sprayed at a distance of 15 cm on each side for two seconds (aerosol) or with 4 strokes (pump spray). The tresses are conditioned overnight in a climatically controlled room at 23° C. and 60% relative atmospheric humidity. One hair tress is a known reference. The hair tresses are labelled with a three-digit code so that the subjects have no knowledge of the product. Each subject receives an individual tress set. The samples are placed in order by the subjects and given a grade. The following properties are graded here:

Stiffness/Flexibility

Grading is on a five-point scale, for example for the flexibility very stiff (1) to very flexible (5), or for the stiffness then for very flexible (1) and for very stiff (5).

Pleasant Soft Hair Feel Before Combing

Grading is on a scale from 1-5 as to how pleasant the hair feed is perceived. From very hard/unnatural (1) to very soft/natural (5).

Rustling (and Breakage of the Polymer Film)

Grading is on a scale from 1-5 as to how loud the polymer film or the setting points breaks/break. From very loud (1) to very quiet (5).

Adhesion: Hold and Crosslinking

The subjects pull the hair tresses apart horizontally and evaluate how well a crosslinking of the hair fibers is constructed by the hair spray and how well this adheres on a scale from 1-5: no crosslinking/short-term hold (1) to very good crosslinking (long-lasting hold=5).

Dry Combability

After assessing the points rustling and adhesion, the hair tresses are combed through using a black comb. The ease of combing is assessed here on a scale from 1-5.

| | |
|---|---|
| 5 | no or only very low resistance upon combing |
| 4 | moderate resistance upon combing |
| 3 | moderate to significant resistance upon combing |
| 2 | considerable resistance upon combing |
| 1 | cannot be combed |

Flaking

During combing, the polymer can be stripped from the hair and fall as residue which looks similar to dandruff formation. Assessment takes place at the same time as the dry combability. The subjects visually assess the appearance of residues on the black comb on a scale from 1-5. From a clear visible residue (1) to invisible residue (5).

Pleasant Hair Feel after Combing

Grading is made on a scale from 1-5 as to how pleasant the hair feel is perceived. From very hard/unnatural (1) to very soft/natural (5).

Static Charging

The hair tresses are conditioned for 2 h in a climatically controlled room at 23° C. and 60% atmospheric humidity. The tresses are then combed through three times in succession rapidly and vigorously. The extent of static charging (fly-away effect) is assessed visually on a scale from 1-5. From considerable fly-away effect (1) to no fly-way effect (5).

Figure 3:
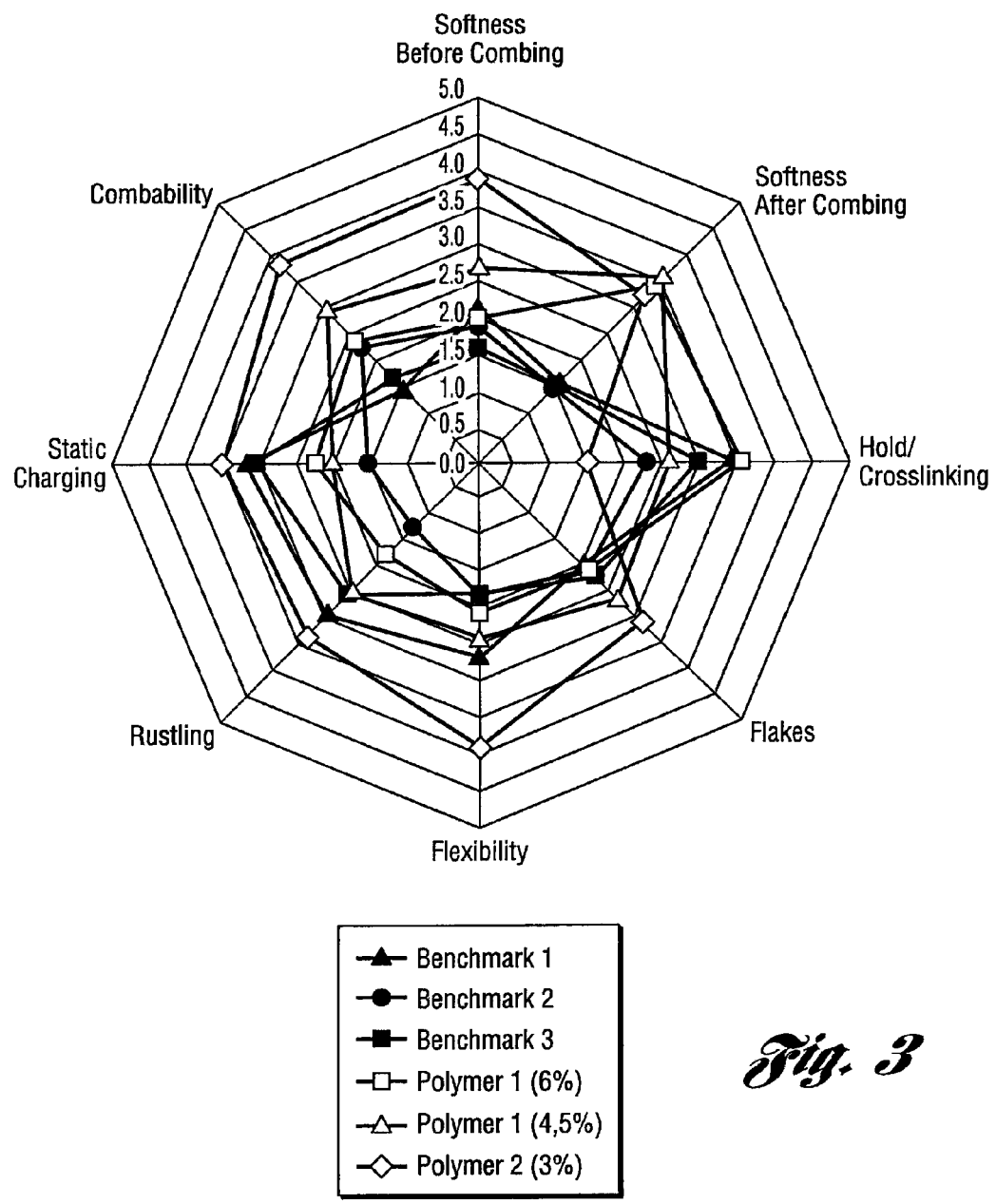
FIG. 3 illustrates the benefits of embodiments of the subject invention regarding a variety of relevant properties after application to hair tresses.

In summary, FIG. 3 is produced from these tests. It shows the result of the comparison of the compositions according to the invention with silicone copolymers 1 and 2 in concentrations of 3% by weight, 4.5% by weight and 6% by weight with commercial products (benchmark 1 to 3). Here, the compositions according to the invention exhibited a significant improvement in the combination of hold, flexibility and soft pleasant feel which constitutes a natural hold. Whereas the commercial products use silicones as conditioners in the formulation in order to be able to attain the indicated behaviour, the silicone copolymers according to the invention can, on account of their hybrid character, be adjusted, by varying the use amount, to a desired profile of hold and feeling of softness.

The invention claimed is:

1. A hair care composition comprising 0.1-12% by weight based on the weight of the hair care composition of at least one silicone copolymer and/or saponification product thereof, the silicone copolymer prepared by copolymerizing monomers comprising A) 0.1-50% based on the weight of the silicone copolymer, of one or more polymerizable silicones of the formula $$R^1R_2SiO(SiR_2O)_nSiR_2R^1 \qquad (1)$$

where
   R is methyl,
   $R^1$ is vinyl, and
   n is 10 to 1000

B) 0.5-14% of one or more copolymerizable unsaturated hydrophilic monomers based on the weight of the silicone copolymer, and C) 30-99.4% of one or more copolymerizable unsaturated hydrophobic monomers based on the weight of the silicone copolymer, the polymerization taking place in the presence of a free radical initiator compound, with the proviso that the molecular weight $M_W$ of the silicone copolymer is 30,000 to 90,000 g/mol and organic polymer chains are covalently bridged by silicone chains derived from said polymerizable silicones A), the hair care composition further comprising 99.9 to 88% by weight of hair care composition components other than the silicone copolymer.

2. The hair care composition of claim 1, wherein the silicone copolymer and/or saponification products thereof contain 0.1-40% by weight of silicone A).

3. The hair care composition of claim 1, wherein the silicone copolymer and/or saponification products thereof contain 0.5-10% by weight of hydrophilic monomer B).

4. The hair care composition of claim 1, wherein the silicone copolymer and/or saponification products thereof contain 3-6% by weight of hydrophilic monomer B).

5. The hair care composition of claim 1, wherein at least one hydrophilic monomer B) is a free-radically polymerizable carboxylic acid selected from the group consisting of crotonic acid and acrylic acid.

6. The hair care composition of claim 1, wherein at least one hydrophobic monomer C) is selected from the group consisting of vinyl esters, and esters of (meth)-acrylic acid.

7. The hair care composition of claim 1, wherein at least one hydrophobic monomer C) is vinyl acetate.

8. The hair care composition of claim 1, wherein A) is present in an amount of from 0.1 to 40% by weight, B) is present in an amount of 0.5 to 10% by weight; and C) is present in an amount of 30-99.4% by weight.

* * * * *